| (12) | United States Patent | (10) Patent No.: | US 9,156,557 B2 |
|---|---|---|---|
| | Penny et al. | (45) Date of Patent: | Oct. 13, 2015 |

(54) ICING SENSOR SYSTEM AND METHOD

(75) Inventors: William Penny, Hampshire (GB); Nicholas Kidd, Hampshire (GB)

(73) Assignee: Penny & Giles Aerospace Limited, Christchurch (GB)

( * ) Notice: Subject to any disclaimer, the term of this patent is extended or adjusted under 35 U.S.C. 154(b) by 184 days.

(21) Appl. No.: 13/140,802

(22) PCT Filed: Dec. 16, 2009

(86) PCT No.: PCT/GB2009/002881
§ 371 (c)(1), (2), (4) Date: Jan. 11, 2012

(87) PCT Pub. No.: WO2010/070273
PCT Pub. Date: Jun. 24, 2010

(65) Prior Publication Data
US 2012/0099616 A1    Apr. 26, 2012

(30) Foreign Application Priority Data
Dec. 18, 2008  (GB) .................................. 0823121.9

(51) Int. Cl.
G01N 25/02  (2006.01)
G01W 1/00  (2006.01)
B64D 15/20  (2006.01)
G01N 25/68  (2006.01)

(52) U.S. Cl.
CPC .............. *B64D 15/20* (2013.01); *G01N 25/68* (2013.01)

(58) Field of Classification Search
USPC ........... 374/16; 73/170.26; 340/580, 581, 284
See application file for complete search history.

(56) References Cited

U.S. PATENT DOCUMENTS

| 3,276,254 | A | * | 10/1966 | Richard | ..................... 73/170.26 |
|---|---|---|---|---|---|
| 3,305,851 | A | * | 2/1967 | Brandtszteter | ................ 340/581 |
| 4,054,255 | A | * | 10/1977 | Magenheim | ................ 244/134 F |
| 4,329,682 | A | * | 5/1982 | Baker | ........................... 340/581 |
| 4,570,881 | A | * | 2/1986 | Lustenberger | ............. 244/134 F |
| 4,980,673 | A | | 12/1990 | Kleven | |
| 5,521,584 | A | * | 5/1996 | Ortolano et al. | .............. 340/581 |

(Continued)

FOREIGN PATENT DOCUMENTS

| CN | 1673035 | 9/2005 |
|---|---|---|
| CN | 101535127 | 9/2009 |

(Continued)

*Primary Examiner* — Harshad R Patel
*Assistant Examiner* — Nasir U Ahmed
(74) *Attorney, Agent, or Firm* — Wells St. John P.S.

(57) ABSTRACT

In a first aspect the invention relates to a sensor system (10) for determining a proximity to icing conditions of an environment. The system includes a sensor having a sensor surface (12) for exposure to the environment, an electrically powered heat pump means (16) for cooling and/or heating the surface (12), and a temperature detector (14) for providing a signal representative of the temperature of the surface (12). An environment temperature is determined, and a processor determines, from the temperature detected by the temperature detector (14) and the environment temperature, a proximity to icing conditions of the environment to which the surface (12) is exposed. In a second aspect of the invention the sensor system includes a power monitor for determining an amount of power required to heat or cool the surface through a temperature indicative of ice formation. The processor determines the proximity to icing conditions from the detected temperatures and the amount of cooling or heating power.

21 Claims, 7 Drawing Sheets

(56) References Cited

U.S. PATENT DOCUMENTS

| | | | |
|---|---|---|---|
| 5,523,959 | A | 6/1996 | Seegmiller |
| 5,709,470 | A | 1/1998 | Finley |
| 6,126,311 | A * | 10/2000 | Schuh ............................ 374/21 |
| 6,328,467 | B1 | 12/2001 | Keyhani |
| 6,456,200 | B1 * | 9/2002 | Bostrom et al. ............. 340/580 |
| 6,870,139 | B2 | 3/2005 | Petrenko |
| 7,000,871 | B2 * | 2/2006 | Barre et al. ................ 244/134 F |
| 7,014,357 | B2 * | 3/2006 | Severson ........................ 374/16 |
| 7,034,257 | B2 | 4/2006 | Petrenko |
| 7,570,760 | B1 | 8/2009 | Olson et al. |
| 7,629,558 | B2 | 12/2009 | Petrenko |
| 7,638,735 | B2 | 12/2009 | Petrenko |
| 7,703,300 | B2 | 4/2010 | Petrenko |
| 8,200,451 | B2 | 6/2012 | Battisti |
| 8,405,002 | B2 | 3/2013 | Petrenko et al. |
| 2003/0155467 | A1 | 8/2003 | Petrenko |
| 2005/0035110 | A1 | 2/2005 | Petrenko |
| 2005/0103927 | A1 | 5/2005 | Barre et al. |
| 2006/0272340 | A1 | 12/2006 | Petrenko |
| 2007/0045282 | A1 | 3/2007 | Petrenko |
| 2007/0198064 | A1 * | 8/2007 | Lapanashvili et al. ............ 607/9 |
| 2007/0267546 | A1 * | 11/2007 | Shah et al. ................. 244/134 F |
| 2008/0196429 | A1 | 8/2008 | Petrenko et al. |
| 2008/0223842 | A1 | 9/2008 | Petrenko et al. |
| 2008/0257033 | A1 | 10/2008 | Roberts |
| 2009/0199569 | A1 | 8/2009 | Petrenko |
| 2009/0235681 | A1 | 9/2009 | Petrenko et al. |
| 2009/0235682 | A1 | 9/2009 | Petrenko et al. |
| 2009/0306928 | A1 | 12/2009 | Battisti |
| 2010/0059503 | A1 | 3/2010 | Petrenko |
| 2010/0084389 | A1 | 4/2010 | Petrenko |
| 2010/0116940 | A1 * | 5/2010 | Picco et al. ................. 244/134 F |
| 2012/0234816 | A1 | 9/2012 | Petrenko et al. |

FOREIGN PATENT DOCUMENTS

| | | |
|---|---|---|
| CN | 201354150 | 12/2009 |
| CN | 2009801569892 | 10/2013 |
| CN | 2009801569892 | 6/2014 |
| FR | 2914906 A1 | 10/2008 |
| RU | 2289892 | 12/2006 |
| RU | 2011129689 | 10/2013 |
| WO | WO 03/069955 | 8/2003 |
| WO | PCT/GB2009/002881 | 4/2010 |
| WO | PCT/GB2009/002881 | 3/2011 |

* cited by examiner

ICING SENSOR SYSTEM AND METHOD

CROSS REFERENCE TO RELATED APPLICATION

This application is a 35 U.S.C. §371 of and claims priority to PCT International Application No. PCT/GB2009/002881 which was filed on 16 Dec. 2009 (16.12.2009), and was published in English, and claims priority to UK Patent Application No. 0823121.9, which was filed on 18 Dec. 2008 (18.12.2008), the teachings of which are incorporated herein by reference.

The present invention relates to a sensor system and method for detecting ice formation, and more particularly for determining how close conditions are to those at which ice will form on a surface.

On aircraft, ice build-up on the wings, propellers, rotor blades, control surfaces etc. can cause the pilot difficulties by adversely affecting aircraft control. Whether or not ice will form depends on the local environmental conditions, such as atmospheric temperature, pressure and moisture content, as well as the speed of the aircraft. Conventionally, ice detectors are employed, which typically look for the presence of ice on an exterior surface of the aircraft so as to generate an indication or warning of the existence of icing conditions. It is a disadvantage that these devices can only detect icing conditions once ice has started to form. They cannot determine how close the conditions are to icing, or whether, or how fast conditions are changing. To ensure the aircraft remains controllable and safe, it is important for the pilot to know what the current air conditions are, how close they are to icing conditions, and whether ice is forming or is likely to form on the aircraft surfaces if no averting action is taken. Conventional ice detectors become particularly ineffective when the air temperature is close to, or just below the freezing point.

U.S. Pat. No. 6,456,200 discloses a device for indicating ice formation, which uses a Peltier element as a temperature difference measuring device. Ice formation is detected through measurement of the change in heat flow due to the release of latent heat during ice formation, which causes a voltage to be generated across a Peltier element.

It is an aim of the present invention to provide a method, a system, and a sensor device for use in such a system that alleviates the aforementioned limitations and disadvantages.

It is a further aim of the present invention to provide a sensor device, which will allow the system to determine proximity to icing conditions. That is to say, a system which can provide an indication of how close the local environmental conditions are to those at which ice will form or whether ice has formed.

According to a first aspect of the present invention there is provided a sensor system for determining a proximity to icing conditions of an environment. The system comprises:

a sensor having a sensor surface for exposure to the environment, an electrically powered heat pump means for cooling and/or heating the surface, and one or more temperature detectors for providing a signal representative of the temperature of the surface;

means for determining an environment temperature; and a processor for determining, from the temperature detected by the temperature detector and the environment temperature, a proximity to icing conditions of the environment to which the surface is exposed.

According to a second aspect of the present invention there is provided a sensor system for determining a proximity to icing conditions of an environment. The system comprises:

a sensor having a sensor surface for exposure to the environment, an electrically powered heat pump means for cooling and/or heating the surface, and a temperature detector for providing a signal representative of the temperature of the surface;

a power monitor for determining an amount of power required to heat or cool the surface to a temperature indicative of ice formation; and a processor for determining, from the detected temperatures and the amount of cooling or heating power, a proximity to icing conditions of the environment to which the surface is exposed.

In embodiments of the first and second aspects, the means for cooling and/or heating comprises a heat pump. Preferably the heat pump is a bidirectional heat pump for example a Peltier heat pump or other fluid based heating and cooling devices. Advantageously, the means for cooling further comprises a heat sink.

Preferably, the temperature detector comprises one or more thermometers or thermocouples. More preferably, the thermometers include platinum or nickel resistance thermometers.

In an embodiment of the invention, the sensor is configured for use on an aircraft so that the sensor surface lies flush with a surface of the aircraft, such as an aircraft skin or wing. In an alternative embodiment the sensor surface forms part of a structure mounted on an aircraft, such as a strut or a fin.

The sensor surface may lie substantially perpendicular to the direction of airflow over the aircraft. Alternatively, the sensor surface may be substantially parallel to the direction of airflow over the aircraft. It is an advantage that the device may be employed to determine icing conditions either in a region of flow stagnation, or in a laminar boundary layer region. Alternatively, the sensor surface may be orientated at an angle to the direction of airflow over the aircraft to aid moisture capture and to aid ice or moisture shedding from the sensor surface.

In embodiments of the invention, the sensor system may comprise a plurality of sensors each having a surface for exposure to the environment, wherein the processing means determines the proximity to icing conditions from the detected temperatures and/or the amount of cooling or heating power to each of the plurality of sensors.

In embodiments of the invention, the processor may be configured to determine an icing severity.

According to a third aspect of the present invention there is provided a method of determining a proximity to icing conditions of an environment, comprising the steps of:

providing a surface exposed to the environment;
cooling or heating the surface;
monitoring the temperature of the surface;
determining a temperature indicative of ice formation;
determining an environment temperature; and
determining, from the monitored temperatures and the environment temperature, a proximity to icing conditions of the environment to which the surface is exposed.

The proximity to icing conditions may have a value defined as the difference between the environment temperature and the temperature indicative of ice formation. The environment temperature may be a prevailing air temperature. The environment temperature may be determined from a temperature of the sensor surface when not cooling or heating, may be determined from an independent temperature sensor or may be provided by other aircraft systems.

When the local environmental conditions are warmer than the conditions where ice is expected to form, the value given to the determined proximity may have one polarity, for example positive, whilst the proximity value may be indicated as negative if the conditions are already in icing. The magnitude of the proximity value gives an indication of how close the icing threshold is, that is the point at which ice will or will not form. When already in icing conditions, the magnitude of the icing proximity gives an indication of how far the conditions need to change to exit icing.

According to a fourth aspect of the present invention there is provided a method of determining a proximity to icing conditions of an environment, comprising the steps of:
  providing a surface exposed to the environment;
  cooling or heating the surface;
  monitoring the temperature of the surface;
  determining an amount of power required to heat or cool the surface to a temperature indicative of ice formation; and
  determining, from the monitored temperatures and the amount of heating or cooling power, a proximity to icing conditions of the environment to which the surface is exposed.

Preferably, the method further comprises determining an icing potential as an indication of a time to, or a likelihood of icing conditions arising or if icing conditions are already present, the icing potential can be an indication of a time to, or likelihood of, icing conditions ceasing or being exited. The icing potential may be determined by measuring the rate of change and direction of the proximity to icing conditions.

In an embodiment of the invention, the cooling or heating of the surface is performed with a known or substantially constant power. The temperature indicative of ice formation may be determined by measuring the variation of temperature with time and detecting a plateau or change in direction in the variation of temperature with time resulting from the latent heat of ice formation.

In an alternative embodiment, the step of cooling or heating the surface comprises controlling the cooling or heating to provide a known or substantially constant rate of change of temperature per unit time. The temperature indicative of ice formation may be determined by monitoring the cooling or heating power with time to detect the temperature at which a change in the power occurs resulting from the latent heat of ice formation.

In embodiments of the invention, the method may comprise alternately cooling and heating the surface. The proximity to icing conditions may be determined both when the surface is heated and when it is cooled. The method may comprise repeating the alternating heating and cooling continuously.

In a preferred embodiment, the method further comprises the step of determining a severity of icing. Preferably the step of determining the severity of icing comprises measuring the magnitude and duration of an increase in temperature when ice formation occurs during cooling.

It is an advantage that as well as being given information on the proximity to icing conditions, the pilot can be made aware of the severity of the conditions. The need to take averting action may be influenced by the severity of the conditions. Also, the effectiveness of any averting action taken will be reflected by a change in the severity. The severity may be provided as a categorized output, for example none, light, moderate or severe icing, or may be provided numerically for example as a liquid water content value.

An ice detection system as described above provides particular advantages over traditional ice detection systems. It is able to provide information to an aircraft pilot about the proximity to icing conditions as the aircraft flies through varying environmental conditions. This is particularly important because the conditions may cause ice to form at certain surface locations on the aircraft without ice being formed at the specific location of a traditional sensor, which the sensor and consequently the pilot would be unaware of. However, circumstances can arise where different local environmental conditions exist at different surface locations, for example due to local variations in pressure.

Whilst an aircraft or helicopter is maintaining forward flight, a continuous and steady airflow is present at the sensor, which is desirable to allow the sensor to rapidly and accurately detect changes in the environment to which it is exposed. However, when a helicopter is hovering, the forward airspeed is no longer providing such air flow over the sensor and as such response time and accuracy will be degraded. Traditional sensors generally use engine bleed air to maintain air flow over the sensor even when hovering, to allow continued sensing. Use of bleed air is not desirable as it draws energy from the engine, is more complicated to install and the bleed air is inherently hot, which detracts from trying to detect ice formation.

Accordingly, in accordance with a fifth aspect of the present invention there is provided an ice detection system comprising:
  a rotating surface;
  a sensor mounted to the rotating surface, wherein the sensor comprises temperature detection means for determining a temperature of the rotating surface and a temperature of an environment through which the surface rotates; and
  a processor for determining a proximity to or presence of icing conditions based on the detected temperatures.

The rotating surface may, for example, be a surface of a rotor, propeller, or turbine vane.

It is an advantage that, by mounting the sensor to (i.e. on or in) the rotating surface, a means is provided to create a continuous air flow over the sensor for ice detection without the need for a separately generated flow, such as bleed air.

In embodiments of this fifth aspect, the system may further comprise features of the first or second aspects, or embodiments thereof.

Embodiments of the invention will now be described by way of an example with reference to the drawings, in which.

Figure 1:
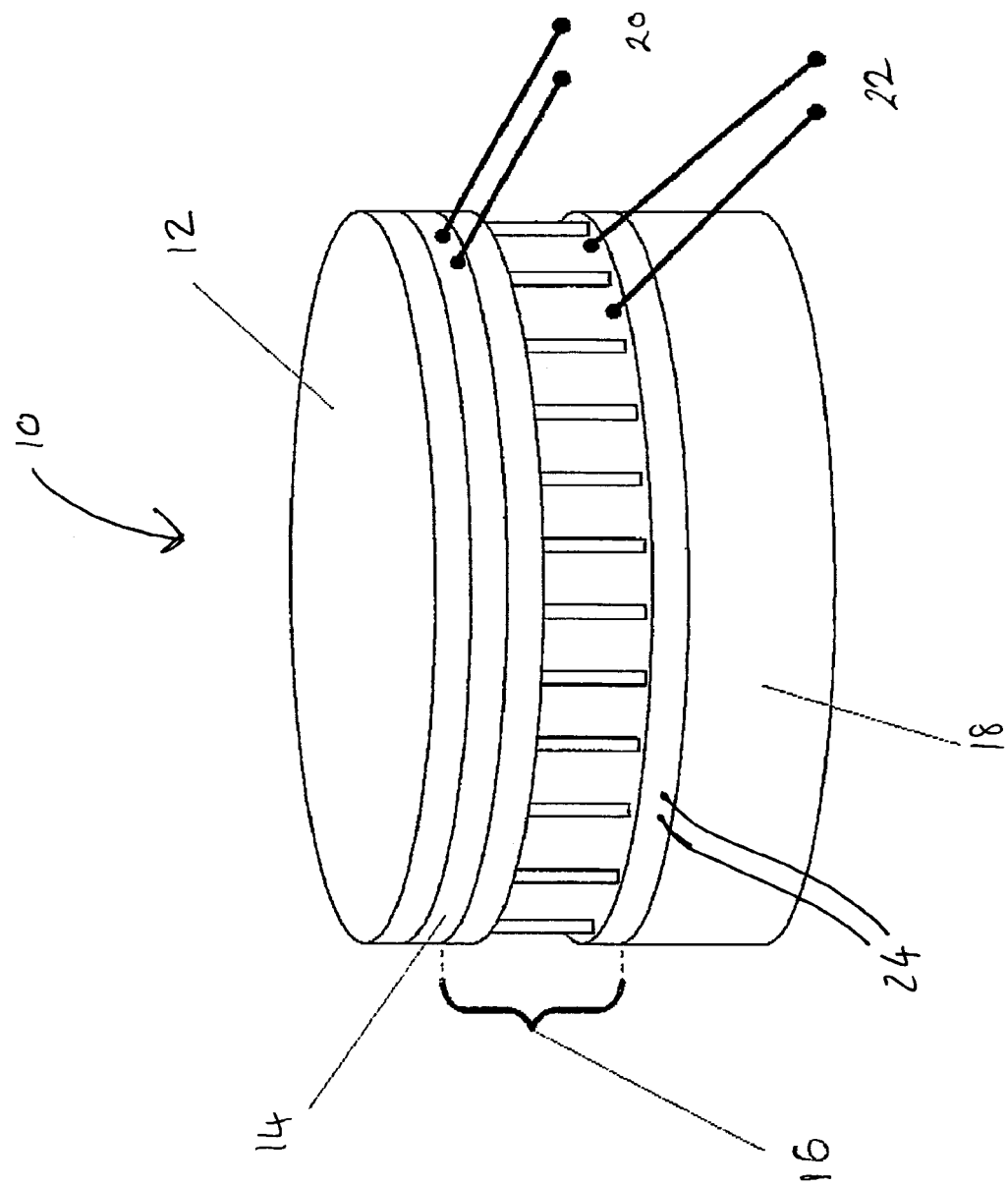
FIG. 1 is a perspective view of a sensor device according to the present invention.

Referring to FIG. 1, a sensor device 10 comprises a surface 12 which is exposed to the surrounding environment. The sensor device 10 further comprises means 16 for cooling or heating the exposed surface 12. This is a bidirectional heat pump 16, for example a Peltier heat pump, and is electronically controlled by a controller (not shown) via heat pump wires 22. A heat sink 18 is provided for use with the heat pump 16, to dissipate heat into the surrounding air or aircraft structure. A temperature detector 14, forming part of, or situated just behind, the surface 12 outputs temperature readings indicative of the temperature of the surface 12 to an acquisition system (not shown) via temperature sense wires 20. The outer surface 12 may be formed of a material that provides physical protection to the sensor 10 and/or temperature detector 14, for example protection from abrasion. The outer surface 12 may be part of the sensor 10 or temperature detector 14, or may be a protective covering placed over the sensor 10 or temperature detector 14. Optionally, a plurality of temperature detectors may be employed, providing a plurality of temperature readings, which may be averaged by the acquisition system. A second temperature detector 24 is optionally provided to monitor performance of the heat pump 16.

Figure 2:
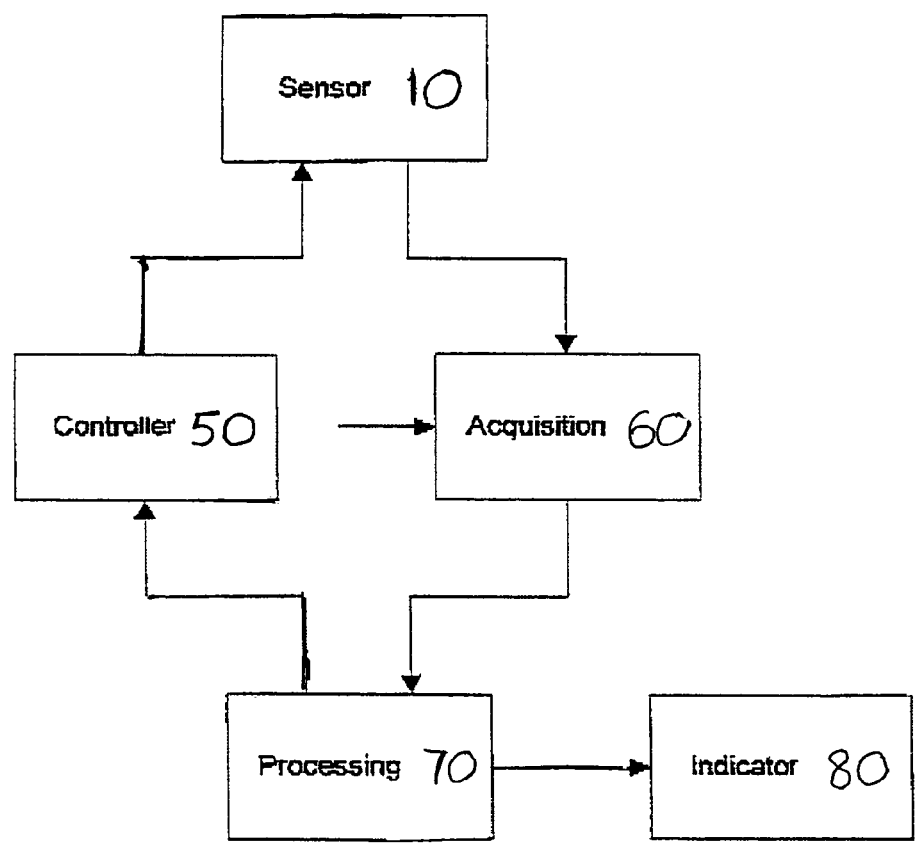
FIG. 2 is a diagram showing the interrelationship between the sensor device of FIG. 1 and other components of a system according to the present invention.

Referring to FIG. 2, a system for determining proximity to icing conditions comprises a sensor device 10 as shown in FIG. 1. A controller 50 is provided to electronically control the heat pump 16 via the heat pump wires 22 to heat or cool the exposed surface 12. The temperature readings from the temperature detector 14 are outputted to an acquisition system 60 via the temperature sense wires 20. A processing device 70 is provided to process the temperature readings from the acquisition system 60, and the results are outputted to an indicator 80 or other aircraft system.

In use, the controller 50 electronically controls the heat pump 16 to heat or cool the surface 12. The temperature detector 14 monitors a temperature that is indicative of that of surface 12 and the temperature sense wires 20 provide temperature readings to the acquisition system 60. The processing device 70 processes the temperature readings from the acquisition system 60 in a manner that will be described in more detail below, and provides the indicator 80 with information indicative of the likelihood of ice formation. The processing device 70 then instructs the controller 50 to heat or cool the surface as appropriate, to allow the measurement of the likelihood of ice formation to be repeated.

When the air temperature is above that at which ice forms on the surface 12, the sensor device 10 is operable to predict how near the current flight conditions ("prevailing air conditions") are to the conditions in which ice is likely to form on the surface 12 ("surface icing conditions"). In this case, the controller 50 instructs the heat pump 16 to cool down the surface 12. Provided there is sufficient water content of the surrounding atmosphere, ice will eventually form on the cooled surface 12. The difference between the prevailing air temperature and the temperature at which ice forms on the surface 12 is a measure of the proximity to icing conditions. Alternatively the quantity of heat removed that causes icing to occur (i.e. the amount of cooling required to form ice), provides a qualitative measure of how near the prevailing air conditions are to surface icing conditions, i.e. the "proximity to icing conditions". If the prevailing conditions are close to freezing, then it is possible that ice may be forming on part of the aircraft, although not at the sensor location. In these circumstances, the proximity to icing conditions determined from the sensor will provide the pilot with an indication that the aircraft may be in danger from ice formation. This is a significant improvement over a conventional ice detector, which can provide no indication of how close the aircraft is to icing conditions nor whether conditions are potentially suitable for the formation of ice, nor whether ice may already be forming on the aircraft but is not able to be detected. Further, the sensor provides a positive determination that icing conditions exist or conditions that may be suitable for icing exist, irrespective of whether visible moisture is present or not.

After ice has accumulated on the surface 12, and a measurement made of the proximity to icing conditions, the controller 50 controls the heat pump 16 to heat the surface 12 up again. As the ice melts, another measurement of the proximity to icing conditions is made by measuring the difference between the temperature indicative of that at which ice forms on the surface 12 and the prevailing air temperature, or by measuring the amount of heating required to melt the ice that has formed. When the temperature of the surface 12 reaches the desired value, (e.g. the previous temperature of the surface before cooling and subsequent heating, or the ambient air temperature, or the maximum temperature that can be reached with maximum power to the heat pump or a defined temperature of operation) the cooling process is started again and the process of determining icing proximity as described above is repeated. This enables the system to continually monitor and update the proximity to icing conditions and the icing severity.

When icing conditions exist the prevailing environmental conditions are such that ice will form on the surface without any cooling by the heat pump 16 being necessary. In these conditions, the controller 50 controls the heat pump 16 to heat the surface 12 and the amount of heating required to melt the ice that has formed gives a measure of the amount of ice that has formed. Cooling is still used however, to provide a more timely response and to give another measure of the amount of ice that has formed. This information can be useful to the pilot who can take action to bring the aircraft out of the icing conditions, or provide an input for triggering a de-icing system.

Figure 3:
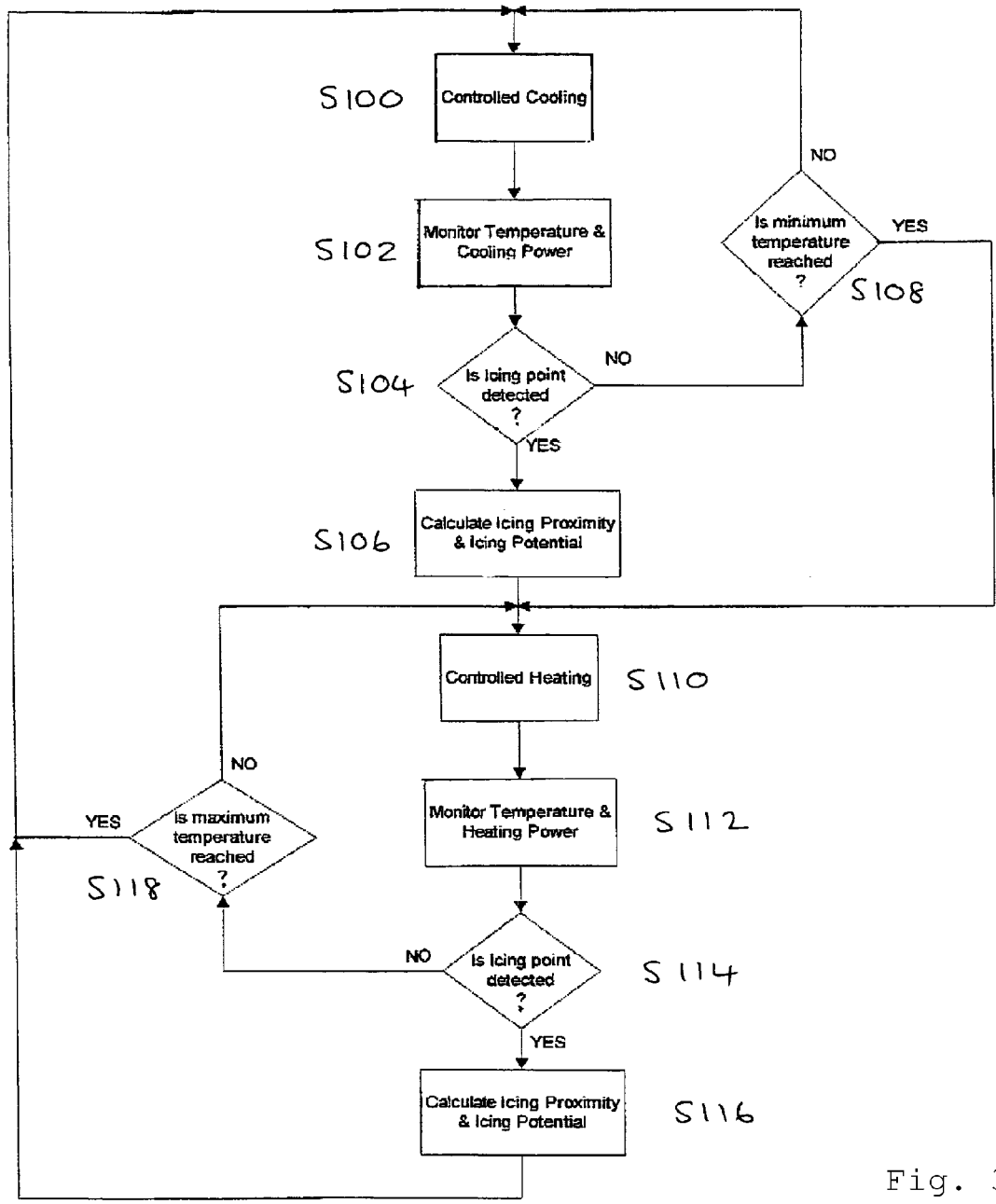
FIG. 3 is a flow chart of the operation of the sensor device of FIG. 1.

FIG. 3 is a flow chart showing the typical steps followed in the operation of the sensor device 10 as shown in FIG. 1, in the system of FIG. 2.

At step S100, with the surface 12 or air temperature above that at which ice would normally form on the surface 12, the surface 12 is cooled down by operation of the heat pump 16. This cooling is a controlled process and is performed for example with the heat pump 16 operating with a known or constant power, or to provide a known or constant rate of temperature decrease with time. As it is cooled, the temperature of the surface 12 is monitored by the temperature detector 14 in step S102. The "cooling power", that is the amount of cooling required to reduce the temperature from the starting (e.g. ambient air temperature) to the temperature measured at that time, is also monitored, at step S102.

When the temperature of the surface 12 is low enough for ice to start to form on it, latent heat will be removed at the point where water changes state to form ice. This is the "icing point", and is characterised by the requirement of a continued removal of heat without any observed overall change in temperature.

Figure 4:
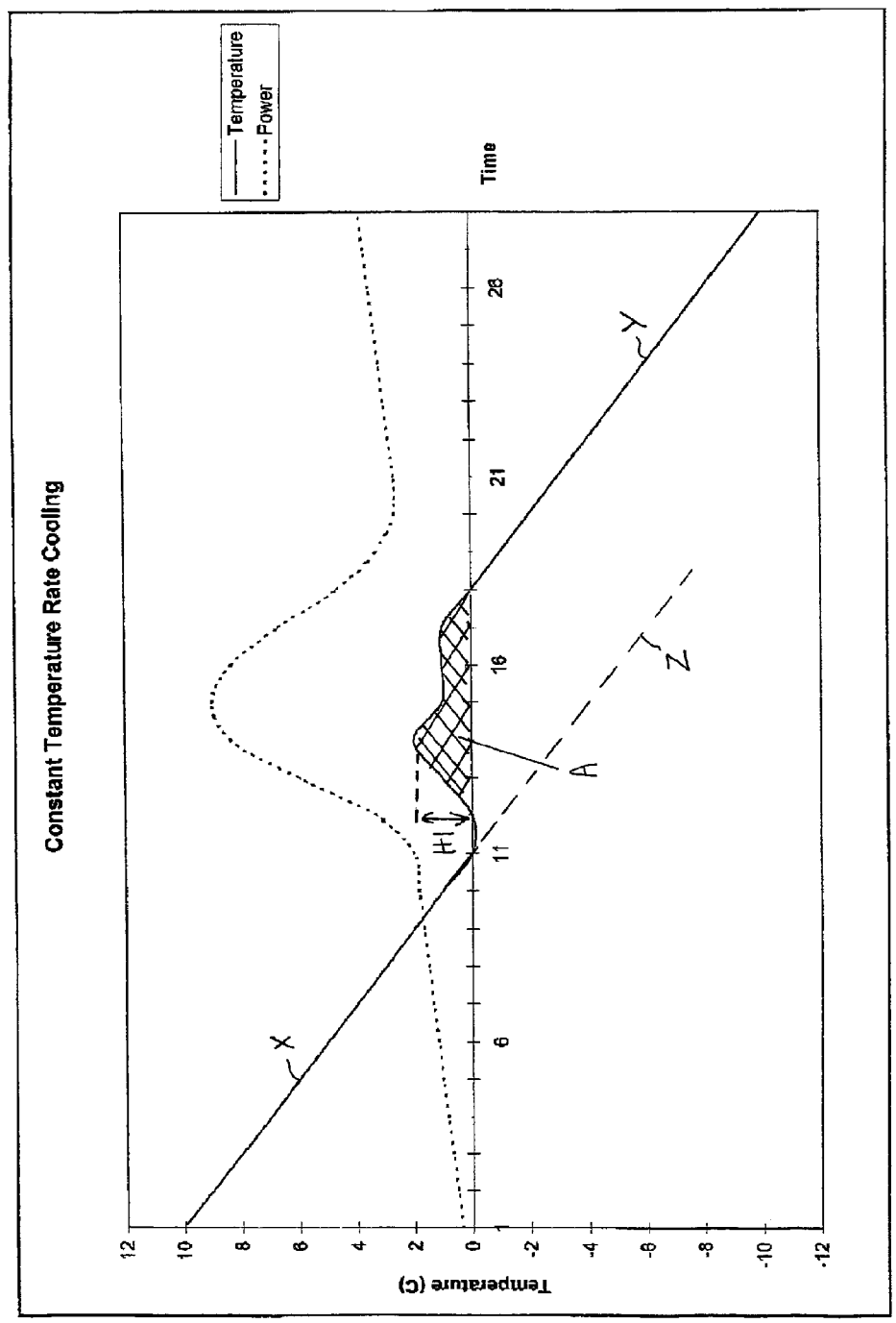
FIG. 4 is a graph showing temperature and heat pump power variation with time while attempting a constant temperature rate cooling of the sensor device of FIG. 1.

FIG. 4 shows the variation in temperature and power as a function of time, with the heat pump being controlled to attempt to cool at a constant temperature rate. The initial cooling follows the line of the graph at X in FIG. 4, which shows that when the temperature reaches that at which ice forms (0° C. in the example shown) the temperature of the surface 12 typically increases slightly before flattening into a plateau. (This situation arises because the rate at which the water gives up its latent heat when freezing initially exceeds the controlled cooling rate of the heat pump. But as the layer of ice formed thickens, this provides some insulation so that the rate at which latent heat is given up reduces.) This region (region 'A') between the point at which the temperature first reaches 0° C. to when it again reaches 0° C., represents the removal of latent heat. The area/magnitude of region A provides an indication of the severity of icing conditions. Subsequently, the temperature continues to fall steadily as shown by the line of the graph at Y, with essentially the same gradient as before the icing point. It will be appreciated that ice will not necessarily start to form at 0° C., but may form at a different temperature depending on the local pressure, airflow and moisture content of the air. As shown in FIG. 4, if there is no moisture in the air, then no ice will form so the line of the graph will pass straight through 0° C. to follow the line of the graph at Z.

Since the increase and plateau at region A in the temperature/time graph of FIG. 4 is characteristic in shape, and deviates significantly from the approximately constant or known temperature gradient observed before and after the icing point, the processing device 70 uses this temperature information to determine the onset of ice formation.

Referring again to FIG. 3, if the icing point is detected at step S104, i.e. the temperature has decreased enough for ice to form upon the surface, then the proximity of the prevailing air conditions to surface icing conditions is calculated at step S106. The proximity to icing conditions has a value defined as the difference between a first temperature and the temperature indicative of ice formation. The first temperature may be a prevailing air temperature. Alternatively, the first temperature may be the temperature of the surface at the start of the cooling step.

In addition, an "icing potential" is calculated. This is defined as the rate of change, and direction, of the icing proximity, and it provides an indication, or prediction, of the time to, or likelihood of, the aircraft experiencing icing conditions.

A measure is also made of the "icing severity" as mentioned above, which is calculated from the magnitude of the temperature rise (due to the release of latent heat) during cooling, i.e. 'H1' in FIG. 4, or the area 'A' under the temperature curve between the time when the temperature first reaches 0° C. (or the icing point when ice first forms) and when the temperature curve next passes through 0° C. (or the icing point).

If the icing point is not detected at step S104 of FIG. 3, i.e. if the temperature is not yet low enough for ice to form on the surface or if there is not enough moisture in the atmosphere, a determination is made instead as to whether a predetermined minimum temperature has been reached at step S108 (or a maximum power condition in which there is no further change in temperature while the heat pump continues to operate at maximum power). If that is not the case, the process returns to step S100, to continue cooling the surface 12.

If either the icing point is detected at step S104 and subsequently the icing proximity and icing potential have been calculated at step S106, or the minimum temperature (or maximum power condition) has been reached at step S108, the surface is heated up again at step S110 at a known or substantially constant temperature (or known or substantially constant power) rate. Again the temperature of the surface 12 is monitored by temperature detector 14 at step S112. The "heating power", that is the amount of heating required to increase the temperature from the surface icing temperature or predetermined minimum temperature back up to the prevailing air temperature (or maximum desired or attainable temperature), is also monitored at step S112.

If ice had previously formed on the surface 12, then during this heating of the surface 12 it will melt. This is equivalent to another icing point being detected, as latent heat is given to the ice to aid melting. Therefore if an icing point is detected during heating, another measurement of the icing proximity and icing potential is made at step S116. The temperature profile observed during heating is inverted relative to the one observed during cooling and is shown in FIG. 5B. The quantity of heat provided gives an indication of the quantity of ice previously formed and which is now being removed. However, it should be borne in mind that during heating it is possible that once a small layer of ice adjacent the heat pump surface 12 has melted, the ice on top of this may simply be blown away. In that case the quantity of heat provided may not be a reliable indicator, unless only a small amount of ice is allowed to form, or the measured values are compensated to allow for this effect. Alternatively, it may be better to just rely on the measurement of icing severity from the cooling cycle.

These additional measurements are either used as a cross check, or an average value of the cooling and heating measurements S106, S116 is taken. After the measurements have been made, the cooling process S100 is started again, in order to obtain further measurements of the icing proximity and icing potential. The process of cooling and heating and taking measurements as previously described is continuously carried out whilst the aircraft is in use and ice detection is required.

If an icing point is not detected during the heating step S110, and the temperature of the surface 12 has reached a maximum preset value (e.g. the temperature prior to cooling or the ambient air temperature or a defined maximum temperature) or a maximum power condition is reached in which there is no further temperature change, then the cooling process at step S100 is started again. If the maximum temperature has not yet been reached at step S118 then the heating process at step S110 continues until either an icing point is detected at step S114 or the maximum temperature is reached at step S118.

FIG. 4 also shows the variation in power with time, whilst attempting constant temperature rate cooling. At the icing point, a rapid increase in cooling power is required (or a rapid increase of heater power if the ambient temperature is below 0° C.). This occurs with no overall significant change in temperature. This increase in power is representative of the onset of icing conditions and hence gives an indication of the icing proximity and icing potential. The magnitude of the increase could also be used to provide a measure of the icing severity in an analogous manner to that described above for when the surface is being cooled.

Figure 5A:
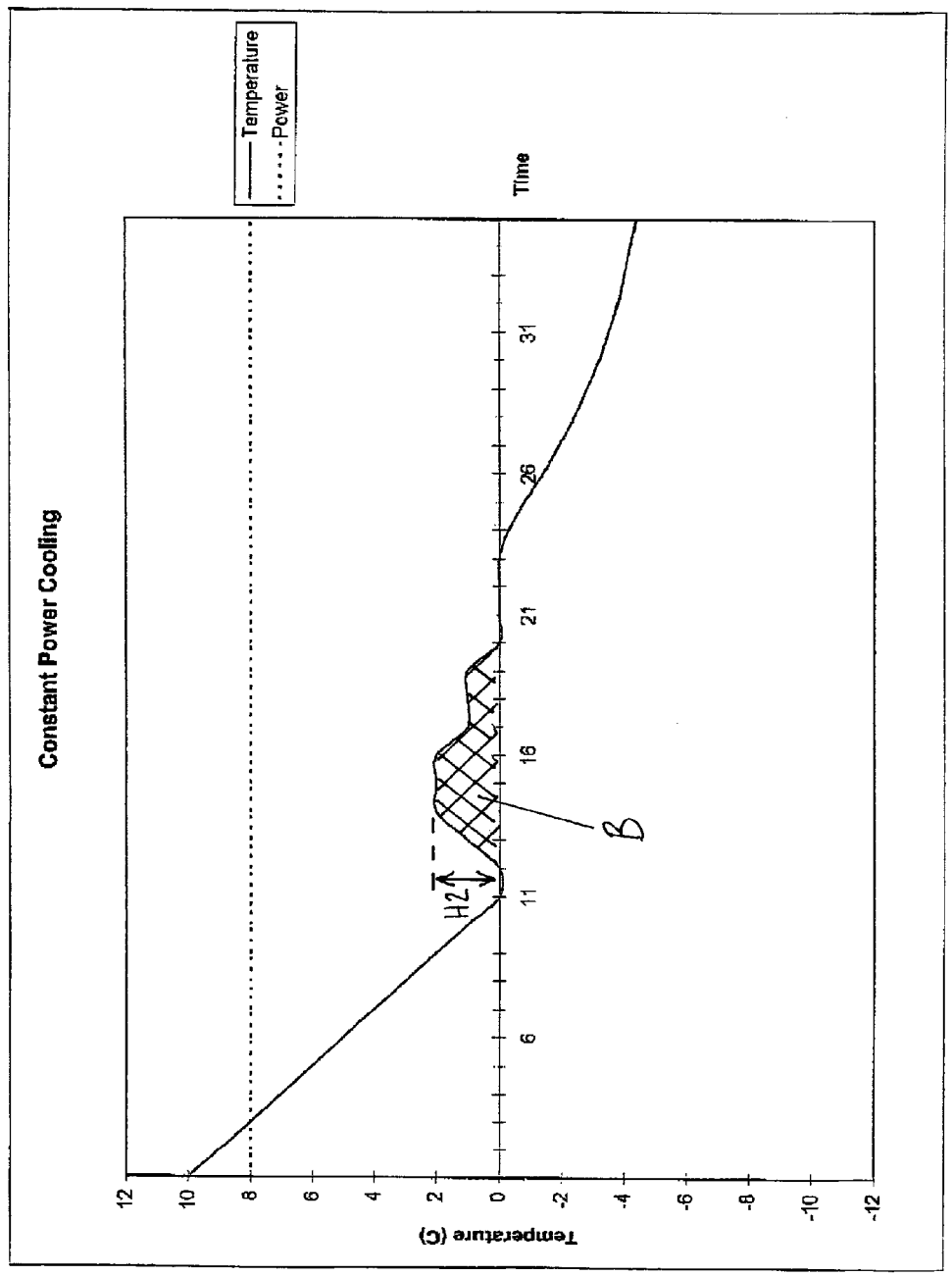
FIG. 5A is a graph showing temperature and heat pump power variation with time during constant power cooling of the sensor device of FIG. 1.
Figure 5B:
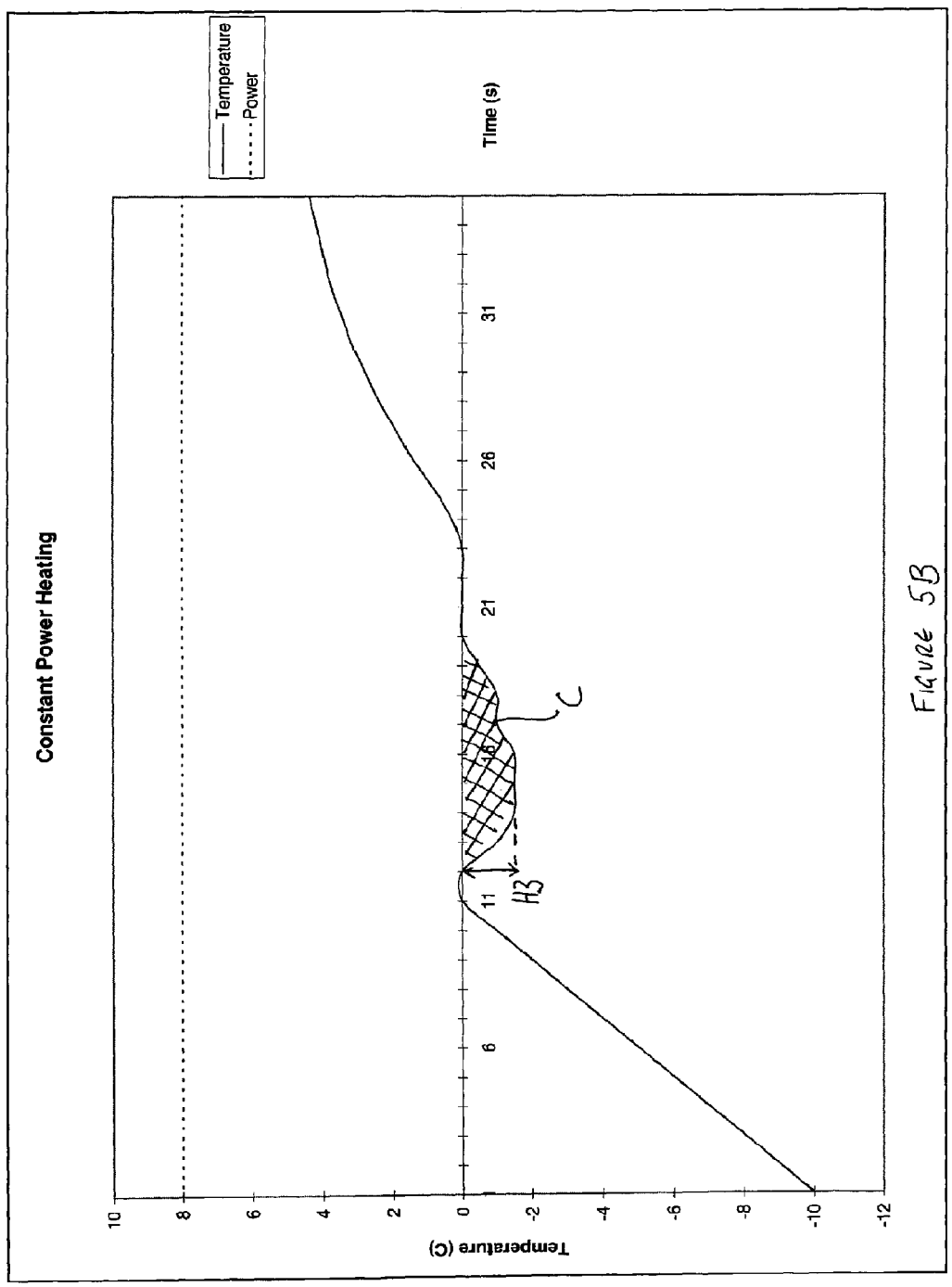
FIG. 5B is a graph showing temperature and heat pump power variation with time during constant power heating of the sensor device of FIG. 1.

FIG. 5A shows the variation in temperature and power with time, with the cooling performed at a known or substantially constant power (compared with attempting the constant temperature rate cooling of FIG. 4). A similar increase and plateau in the temperature curve are again observed as latent heat is released as ice starts to form. The icing proximity and icing potential are determined in a manner similar to that described above for the constant temperature rate cooling. The magnitude of the temperature rise 'H2', or the area B-are representative of the release of latent heat, and can be used to provide a measurement of the icing severity.

The sensor device 10 also operates as a conventional ice detector, if ice has already formed on the surface 12 being monitored. If the surface is heated to melt the ice, latent heat will be required for the phase change, providing a detectable temperature reversal and/or plateau. FIG. 5B shows the variation in temperature with time for the case where the surface is being heated at a known or substantially constant power, with the temperature reversal shown as H3 and the area under the plateau curve as C. The characteristics of this temperature reversal or plateau provide a measurement of the icing severity as described above.

Figure 6:
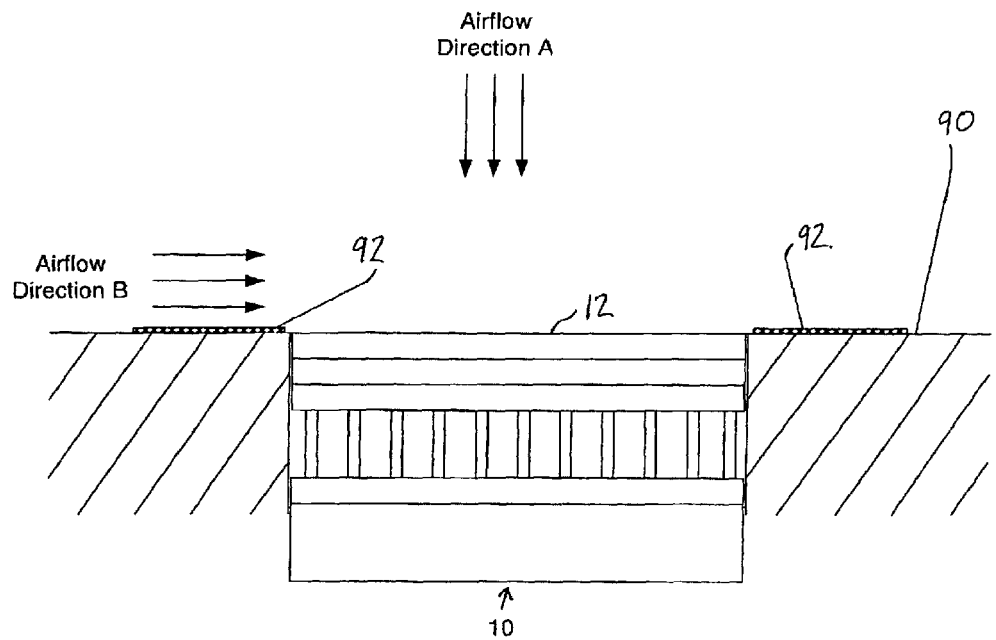
FIG. 6 is a sectional view of the sensor device of FIG. 1 embedded in an exterior surface of an aircraft.

Referring to FIG. 6, the sensor device 10 of FIG. 1 is shown embedded in an aircraft surface 90. The exterior surface 12 of the sensor device 10 is preferably level and flush with the exterior aircraft surface 90 in which it is embedded. The aircraft surface 90 is typically an aircraft wing or skin or engine nacelle, or part of a new strut or fin provided for the purpose of ice detection and prediction. Alternatively, the device 10 could be mounted such that the exterior surface 12 is proud of or recessed in to the aircraft surface 90. The device could also form part of a structure mounted to the aircraft. Alternatively, the device 10 could be incorporated into a housing with a flow passage through which air may be induced to flow (for example using bleed air from the aircraft engine system). A sensor of this type may be particularly useful at low air speeds or where the aircraft (e.g. a helicopter) is hovering. Alternatively, the device 10 could be incorporated into a housing that is moving or rotating as part of a new or existing aircraft system, such that air flow over the device 10 is maintained or created to allow detection at low air speeds or when hovering (e.g. the device is mounted to a rotating part of the rotor head or blades of a helicopter, such as the power distribution section of a rotor ice protection system)

The positioning of the sensor device 10 relative to the air flow around the aircraft is important to the effectiveness of the prediction/detection system. The orientation of the sensor device 10 to the airflow determines the conditions being detected. If the sensor device 10 is mounted on the leading edge of the aircraft structure, air flows in the direction 'A' and so the sensor senses the conditions at the air stagnation point, which is typically at a higher temperature than ambient. The leading edge may be flat or curved. If the sensor device 10 is mounted with air flow direction 'B', the conditions sensed are that within the airflow boundary layer, inside an area of laminar flow. In this case, the sensor device 10 is mounted on the flat surface of a horizontal (e.g. upper or lower surface of a wing) or vertical element of the aircraft structure, which will normally be substantially flat. The device 10 may also be positioned on a surface at any orientation between the substantially vertical and horizontal positions shown in FIG. 6. A suitable orientation and mounting location may be based on the ice build-up characteristics of the aircraft surface, which may depend on the local surface characteristics and aerodynamics, to aid moisture capture and to aid ice or moisture shedding from the sensor surface.

As local pressure and temperature conditions may be different at a stagnation point and in a boundary layer, then for optimum performance, two or more sensor detectors 10 are used, located -at positions determined for optimal performance.

To prevent ice build-up on surrounding surfaces from covering over the device 10, a heater 92 may be provided on the aircraft surface 90 in proximity to the device surface 12. The heater is shown mounted close to, but not contacting the surface 12. The separation of the heater from the device is selected so that heat conduction from the heater into the sensor does not interfere with operation or accuracy of the device 10. Alternatively, or additionally a region of thermal insulation (not shown) may be provided between the heater 92 and the sensor surface 12. Heater 92 and local surface 90 may be provided as part of the assembly including the sensor 10.

The ice detector systems as described above have significant advantages over traditional ice detection systems by providing information to an aircraft pilot about the proximity to icing conditions as the aircraft flies through varying environmental conditions. This is particularly important because the conditions may cause ice to form at certain surface locations on the aircraft without ice being formed at the specific location of a traditional sensor, which the sensor and consequently the pilot would be unaware of. However, as explained above, positioning of the sensor is important because different local environmental conditions can arise at different surface locations such as due to local variations in pressure.

Whilst an aircraft or helicopter is maintaining forward flight, a continuous and steady airflow is present at the sensor, which is desirable to allow the sensor to detect changes in the environment to which it is exposed. Whilst a helicopter is in the hover, the forward airspeed of the helicopter is no longer providing such air flow over the sensor and as such response time and accuracy will be degraded. Traditional sensors generally use engine bleed air to maintain air flow over the sensor even when hovering, to allow continued sensing. Use of bleed air is not desirable as it draws energy from the engine, is more complicated to install and the bleed air is inherently hot, which detracts from trying to measure ice. As such, a means to create a continuous air flow over an ice detection sensor without the need for bleed air is advantageous.

Figure 7:
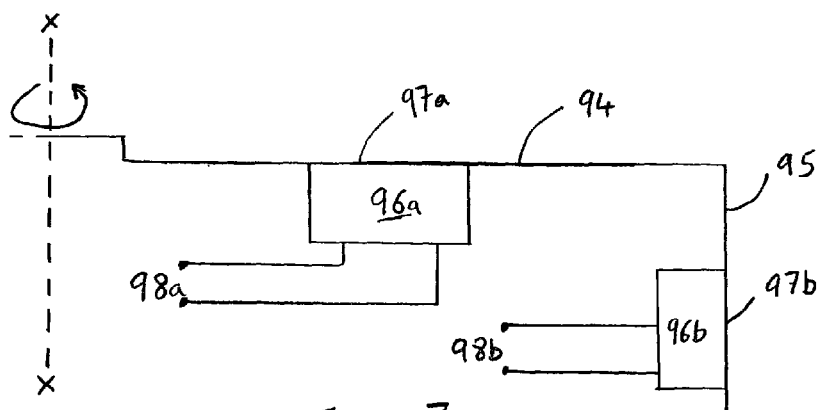
FIG. 7 is a sectional view of an ice detector system in a rotating surface of an aircraft.

FIG. 7 illustrates an ice detection system for surfaces 94, 95, which are being caused to rotate about an axis X-X. Two sensors 96a, 96b are shown by way of example, each mounted to one of the rotating surfaces 94, 95. For example, the surface 94 might be a horizontal surface of part of a helicopter rotor assembly, while the surface 95 might be a radially outward facing surface of the rotor assembly. The principles described below may be applied to a system having just one sensor or many sensors.

The sensors 96a, 96b have respective exposed surfaces 97a, 97b and in the illustrated embodiment are mounted with the surfaces 97a, 97b flush with the rotating surfaces 94, 95. Alternatively, the sensors could be mounted such that the exposed surfaces 97a, 97b stand proud of the surfaces 94, 95, or are recessed below the rotating surfaces 94, 95. The sensors 96a, 96b may be mounted to present the exposed surfaces 97a, 97b at an angle to the direction of movement so that the rotational movement presents an incident "air flow". The sensor surfaces 97a, 97b may be angled at any angle between being parallel with the air flow and being perpendicular to the air flow. The angle may be selected to optimise the sensing efficiency without causing excessive drag. The surfaces 94, 95 may be angled to present the sensors 96a, 96b and the exposed surfaces 97a, 97b at an angle to the direction of movement so that the rotational movement presents an incident "air flow". The surfaces 94, 95 may be angled at any angle between being parallel with the air flow and being perpendicular to the air flow. The angle may be selected to optimise the sensing efficiency without causing excessive drag.

The sensors 96a, 96b each include a temperature detector, such as a thermocouple or resistance thermometer, that determines a temperature of the rotating exposed surface 97a, 97b. The sensors 96a 96b each provide a signal at a respective output 98a, 98b. The sensors 96a, 96b may also include one or more further temperature detectors that monitor a temperature of an environment through which the surface rotates. Alternatively separate sensors may be used to determine the local environment temperature, or this may be provided by other system components. The temperature values (surface and environment) are provided to a processor that determines a proximity to or presence of icing conditions, in a manner similar to that described above. The processor may form part of each sensor 96a, 96b in which case a signal is provided at the respective output 98a, 98b to indicate presence of, or a proximity to icing conditions at the respective rotating exposed surface 97a, 97b. Alternatively, the processing may be performed elsewhere (for example at a central processor, which may or may not be rotating with the sensors 96a, 96b).

The ice detector system may include any or all of the features of the detector systems described above with reference to FIGS. 1 to 6.

Many other applications may benefit from inclusion of such ice detection systems, such as on wind turbines, wind turbine blades, in an air inlet for an engine such as a power generator jet turbine, on an unmanned aerial vehicle or any other application where the presence of or proximity to icing conditions would be beneficial. The device and processing means can also be used as described to determine the humidity level or moisture content of the environment.

The invention claimed is:

1. A method of determining an icing potential of an aircraft in an environment, wherein the icing potential provides an indication, or prediction, of the time to, or likelihood of the aircraft experiencing icing conditions, the method comprising:

providing a sensor having a surface exposed to the environment and thermally coupled to a heat pump;

operating the heat pump to cause heat to flow through the surface;

monitoring a temperature of the surface;

determining a temperature indicative of ice formation on the surface;

determining an environment temperature representative of the temperature of the environment to which the sensor surface is exposed;

determining the value of a difference between the environment temperature and the temperature indicative of ice formation, said value representing a proximity to icing conditions of the environment to which the surface is exposed; and determining the icing potential by measuring a rate and direction of change of the value representing the proximity to icing conditions.

2. The method of claim 1 wherein operating the heat pump to cause heat to flow through the surface comprises operating the heat pump to cause heat to flow away from the surface to cool the surface.

3. The method of claim 1 wherein operating the heat pump to cause heat to flow through the surface comprises operating the heat pump to heat the surface.

4. The method of claim 1 wherein the environment temperature is a prevailing air temperature.

5. The method of claim 1 wherein the environment temperature is determined from a temperature of the surface when not operating the heat pump.

6. The method of claim 1 further comprising determining an indication of a time to icing conditions arising.

7. The method of claim 1 wherein the heat pump is operated with a substantially constant power to cause heat to flow through the surface.

8. The method of claim 1, wherein the temperature indicative of ice formation is determined by measuring the variation of temperature with time and detecting a change in direction in the variation of temperature with time resulting from the latent heat of ice formation.

9. The method of claim 1, comprising controlling the heat pump to provide a substantially constant rate of change of temperature per unit time.

10. The method of claim 1, comprising alternately cooling and heating the surface.

11. The method of claim 10 comprising repeating the alternating heating and cooling continuously.

12. The method of claim 1 further comprising determining a severity of icing by measuring the magnitude of a change in temperature when the surface passes through the temperature indicative of ice formation.

13. The method of claim 1 further comprising determining a severity of icing by measuring the duration of a plateau in temperature when the surface passes through the temperature indicative of ice formation.

14. A method of determining an icing potential of an aircraft in an environment, wherein the icing potential provides an indication, or prediction, of the time to, or likelihood of the aircraft experiencing icing conditions, the method comprising:

providing a sensor having a surface exposed to the environment and an electrically powered heat pump thermally coupled to the surface;

operating the heat pump to cause heat to flow through the surface;

monitoring a temperature of the surface;

determining an amount of power required to cause the surface to pass through a temperature indicative of ice formation;

determining, from the monitored temperatures and the amount of power, the value of a quantity of heat that causes the surface to pass between a predetermined temperature above the temperature indicative of ice formation to a predetermined temperature below the temperature indicative of ice formation, said value representing a proximity to icing conditions of the environment to which the surface is exposed; and determining the icing potential by measuring a rate and direction of change of the value representing the proximity to icing conditions.

15. The method of claim 14 wherein operating the heat pump to cause heat to flow through the surface comprises operating the heat pump to cause heat to flow away from the surface to cool the surface, and wherein determining the value of a quantity of heat determines the quantity of heat required to cause ice to form on the surface.

16. The method of claim 14 wherein operating the heat pump to cause heat to flow through the surface comprises operating the heat pump to heat the surface, and wherein determining the value of a quantity of heat determines the quantity of heat required to melt ice that has formed on the surface.

17. The method of claim 14, wherein the temperature indicative of ice formation is determined by measuring the variation of temperature with time and detecting a change in direction in the variation of temperature with time resulting from the latent heat of ice formation.

18. The method of claim 14, wherein the heat pump is operated to provide a substantially constant rate of change of temperature per unit time.

19. The method of claim 18, wherein the temperature indicative of ice formation is determined by monitoring the power with time to detect the temperature at which a change in the power occurs resulting from the latent heat of ice formation.

20. The method of claim 18, comprising alternately cooling and heating the surface.

21. The method of claim 20 comprising repeating the alternating heating and cooling continuously.

* * * * *